United States Patent
Cegla

(10) Patent No.: US 8,770,984 B2
(45) Date of Patent: Jul. 8, 2014

(54) THERAPEUTIC DEVICE

(75) Inventor: Ulrich Cegla, Montabaur (DE)

(73) Assignee: R. Cegla GmbH & Co. KG, Montabaur (DE)

( * ) Notice: Subject to any disclaimer, the term of this patent is extended or adjusted under 35 U.S.C. 154(b) by 338 days.

(21) Appl. No.: 13/385,362

(22) Filed: Feb. 15, 2012

(65) Prior Publication Data

US 2012/0227741 A1    Sep. 13, 2012

(51) Int. Cl.
*G09B 23/28* (2006.01)

(52) U.S. Cl.
USPC ........................................ 434/262

(58) Field of Classification Search
CPC .............................. G09B 23/28; G09B 23/288
USPC ............. 434/236, 247, 262, 265; 128/200.24; 601/41
See application file for complete search history.

(56) References Cited

U.S. PATENT DOCUMENTS

| 4,325,364 A * | 4/1982 | Evans ....................... 128/201.13 |
| 4,506,883 A * | 3/1985 | Rathbun ......................... 482/13 |
| 4,797,105 A * | 1/1989 | Green ........................... 434/265 |
| 8,100,696 B2 * | 1/2012 | Wezurek et al. .............. 434/390 |
| 8,376,752 B2 * | 2/2013 | McDevitt ...................... 434/262 |
| 8,469,714 B2 * | 6/2013 | Hsiao et al. ................... 434/262 |
| 8,517,740 B2 * | 8/2013 | Trotta et al. .................... 434/267 |

FOREIGN PATENT DOCUMENTS

| DE | 44 16 575 | 11/1995 |
| DE | 10 2008 008 161 | 8/2009 |

* cited by examiner

*Primary Examiner* — Kurt Fernstrom
(74) *Attorney, Agent, or Firm* — Pandiscio & Pandiscio

(57) ABSTRACT

A therapeutic device for improving the respiration of a patient, the device comprising a curved or kinked pipe section, into the first end of which a mouthpiece provided with a passage is disposed, a holding peg inserted into a second end of the pipe section and connected thereto, the holding peg having a passage disposed therein and being insertable into the inside of the pipe section, and a flexible hose attached to the holding peg inside the pipe section, a free end of the hose moveable freely in an area of the mouthpiece between an inner wall of the pipe section, such that the therapeutic device can be used during inhalation and exhalation, the device (1) enabling the patient to train his respiratory passageways both during exhalation and inhalation, thereby to improve the effectiveness of respiration.

11 Claims, 6 Drawing Sheets

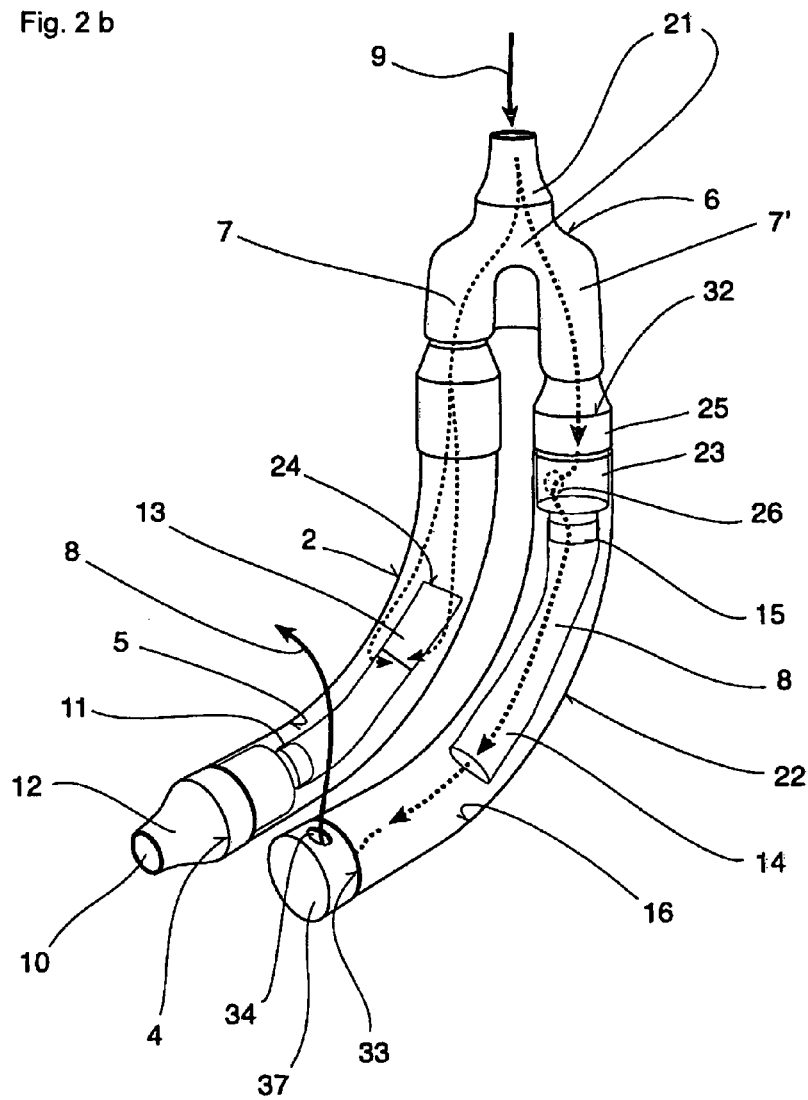

THERAPEUTIC DEVICE

BACKGROUND OF THE INVENTION

1. Field of the Invention

The present invention relates to a therapeutic device.

2. Description of the Prior Art

During exhalation, the person's breath is forced into a hose disposed in the inside of a curved pipe section. The curvature of the pipe section kinks the hose, with the effect that the hose reproduces the curvature of the pipe section and can, as a result, be induced to adopt adjustable and different vibratory conditions.

As a result of the variably adjustable length and rotation of the hose inside the pipe section, it is possible to achieve variable adjustments to the pressure conditions by means of which the hose is induced to undergo oscillating vibrations and, accordingly, the pressure resistance values of the hose can be adapted to the requirements of the particular user. Consequently, this embodiment of the therapeutic device can be used for improving the pulmonary volume and improving the exhalation process in patients ranging from asthma suffers to performance athletes.

Although such respiratory therapeutic devices have proven effective in practice, it has become apparent that there is a significant medical requirement for providing such respiration therapy devices not just for exhalation but also for inhalation.

SUMMARY OF THE INVENTION

The task of the present invention is therefore to provide a respiratory therapeutic device which can be used both during inhalation and exhalation, with the effect that the respiratory therapeutic device enables the patient to train his or her respiratory passageways both during inhalation and exhalation, thereby to improve the effectiveness of respiration.

Furthermore, it is the task of the present invention to provide a respiratory therapeutic device by means of which a user may inhale and exhale at choice or continuously in order to achieve the corresponding therapeutic results without having to put down the respiratory therapeutic device.

Due to the fact that a channel branch is provided in the mouthpiece, it is possible to connect a second pipe section to this, and to have an opening incorporated in this second pipe section which either restricts or releases the emergence of air, thereby establishing adjustable flow conditions and providing an advantageous way of adapting the air resistance to the requirements and the therapeutic results of the user. Consequently, a combination respiratory therapeutic device of this kind can be used both for inhaling and exhaling.

If a further hose is inserted in the second pipe section, this acts as a valve during inhalation, because the resulting pressure conditions inside the second pipe section lead to the effect that the hose is pulled together due to the negative pressure, with the result that no air can pass through the hose. Thus, the hose acts in the same ways as a stop valve.

During exhalation, on the other hand, the hose in the second pipe section is opened out and the respiratory air can flow through it, thus causing the hose to undergo oscillatory vibrations. At the same time, the hose inserted in the first pipe section is pressed together due to the positive pressure prevailing in the inside of the pipe section, and thus functions in the same way as a valve, as a stopper or air closure element. At the same time, the positive pressure prevailing in the first pipe section causes the hose inserted in it to vibrate, with the effect that the user can hear and detect what respiratory results are being produced during inhalation, as a result of the pressure condition that is established and the vibratory behaviour of the first hose which is in a causal relationship with the pressure condition.

BRIEF DESCRIPTION OF THE DRAWINGS

The drawings show a sample embodiment configured in accordance with the present invention, the details of which are explained below. In the drawings.

DESCRIPTION OF THE PREFERRED EMBODIMENTS

Figure 1:
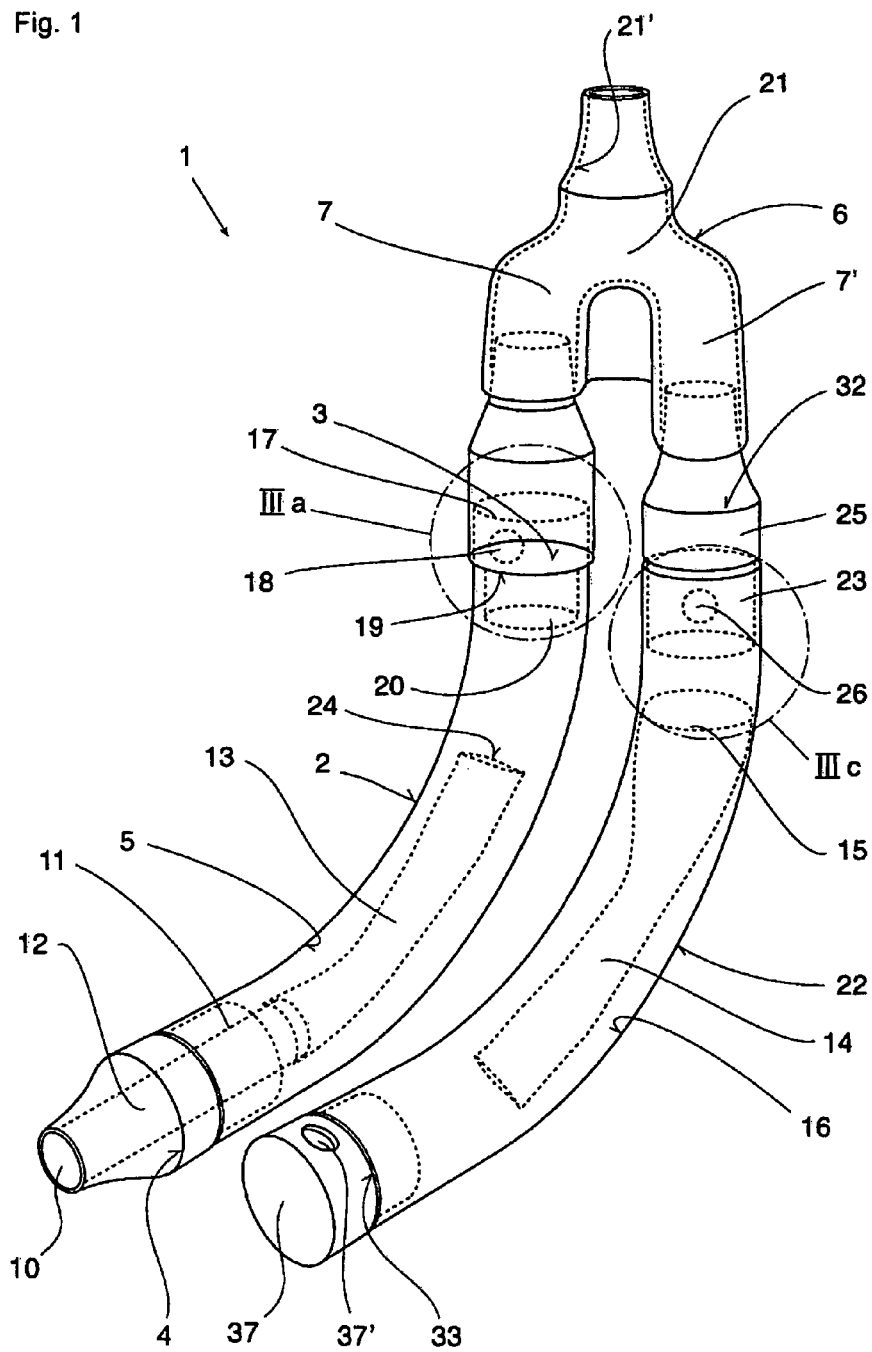
FIG. 1 shows in a perspective view a combination respiratory therapeutic device consisting of two curved pipe sections parallel to one another, in each of which a vibrating hose is arranged in an offset arrangement inside the corresponding pipe section, and a mouthpiece connecting the two pipe sections together within which a channel branch is disposed.
Figure 2:
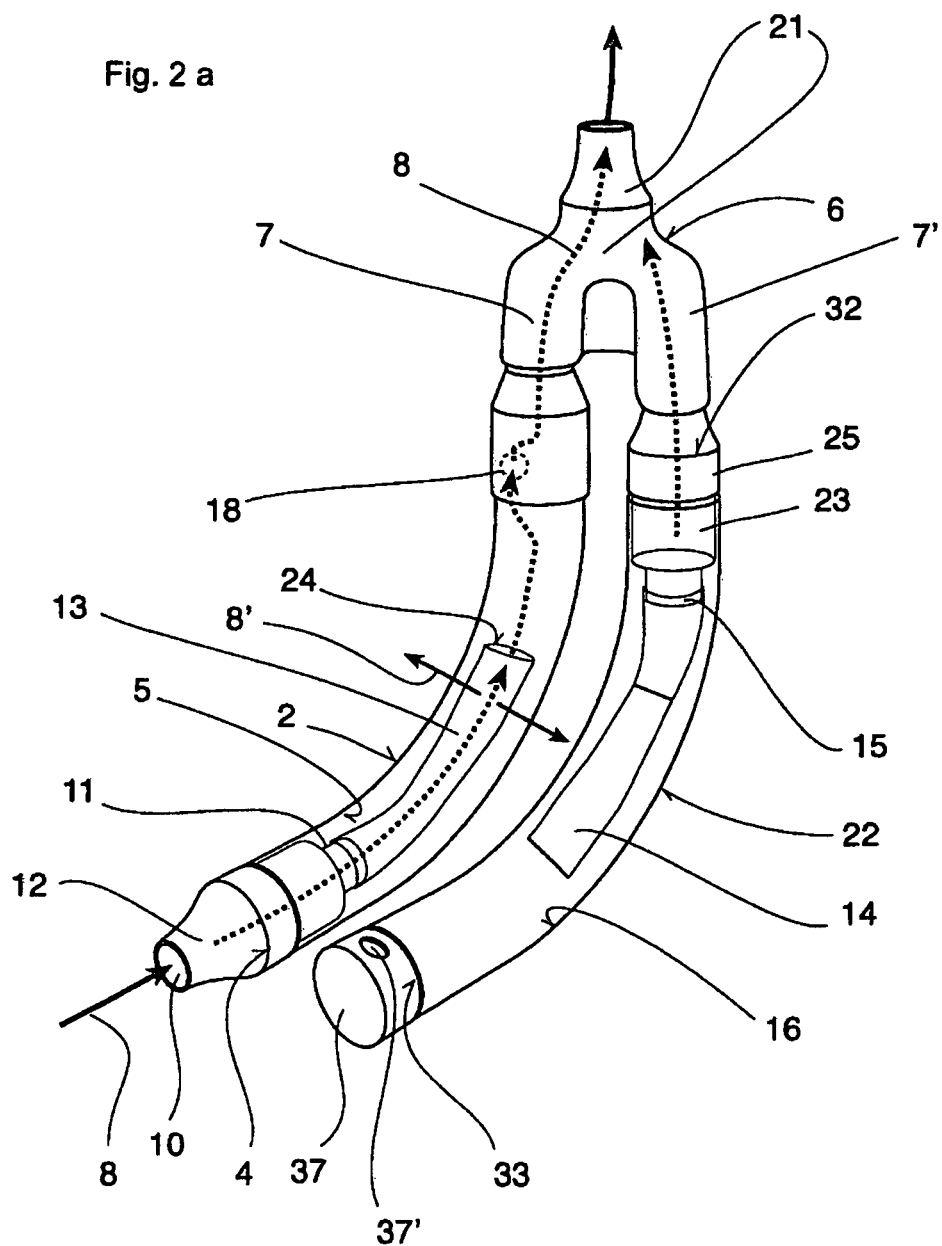
FIG. 2a shows the respiratory therapeutic device in accordance with FIG. 1, in the condition of inhalation and with the resulting flow conditions.
FIG. 2b shows the respiratory therapeutic device in accordance with FIG. 1, in the condition of exhalation and with the resulting flow conditions.

FIG. 1 shows a therapeutic device 1 for improving the respiration of a patient which, in accordance with FIGS. 2a and 2b, can be used simultaneously for inhalation and exhalation, and thus for a combined airway therapy. FIGS. 1, 3a, 3b and 3c are intended to explain the design and structure of the therapeutic device 1, and FIGS. 2a and 2b to explain the mode of function of the therapeutic device 1.

The therapeutic device 1 initially comprises a first pipe section 2 which is curved or kinked. A second pipe section 22 is provided in parallel to the first pipe section 2.

A first end 3 of the first pipe section 2 is provided with a mouthpiece 6 inserted in it or placed on it, by means of which the two pipe section 2 and 22 are connected together. This is because the mouthpiece 6 has a channel branch 21 provided in it, by means of which two air channels 7 or 7' of the mouthpiece 6 which communicate with the two pipe sections 2 and 22 are combined into one output or input channel 21'.

The first pipe section 2 is provided with an inlet opening 10 provided in its second end 4 facing away from the mouthpiece 6, and a holding peg 11 can be attached to the inlet opening 10 in such a way that the holding peg 11 can be positioned in various positions in relation to the second end 4 of the first pipe section 2. This is because the holding peg 11 is provided with a first hose 13 attached to it which is firmly attached to the holding peg 11. The holding peg 11 is provided with a passage channel 12 disposed therein which is in a communicating active connection with the first hose 13 in such a way that the air flowing in through the inlet opening 10 enters the first hose 13, causing it to expand and, given an adequate air flow, leading to oscillating vibrations of the hose 13, with the effect that the hose 13 positioned inside the first pipe section 2, and in this case in particular its free end 24 facing towards the mouthpiece 6, is moved back and forth in between an inner wall 5 of the first pipe section 2.

Figure 3:
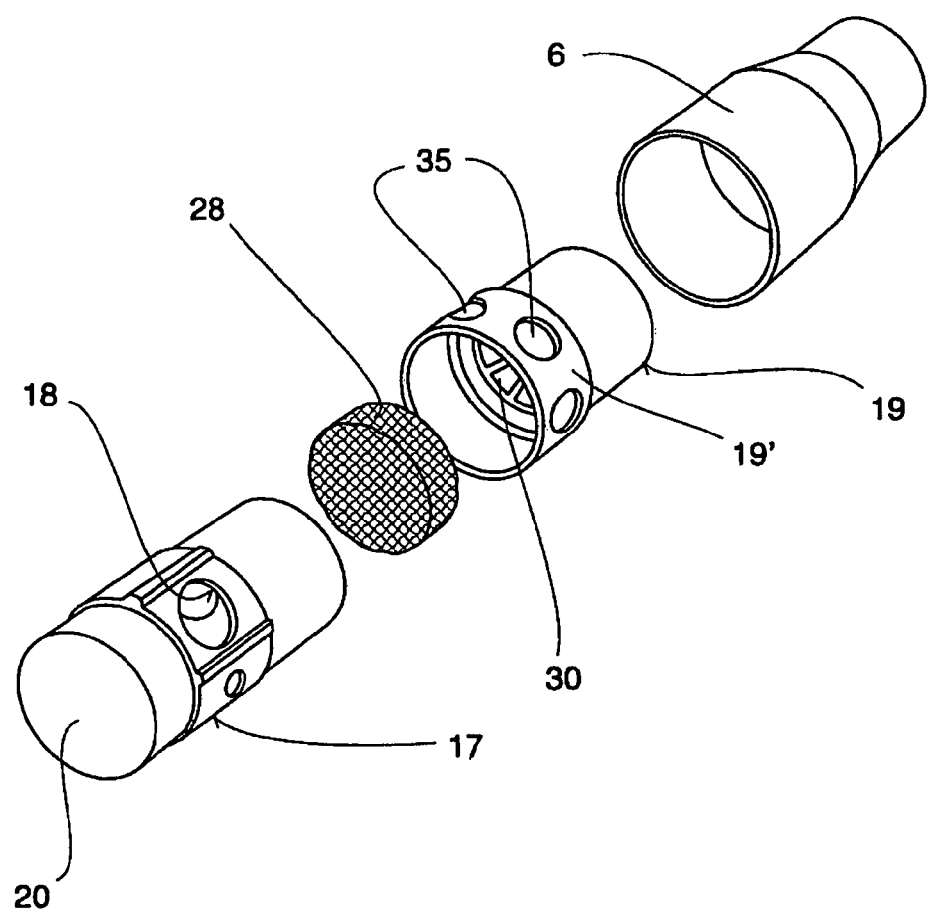
FIG. 3a shows in an exploded view a ring element inserted into the first pipe section in accordance with FIG. 1, with passage openings disposed in the ring element and with an adjustable sleeve for covering the passage openings.
FIG. 3b shows the ring element in accordance with FIG. 3a, in a lengthways and transverse section.
FIG. 3c shows an air distribution element which is inserted in the second pipe section in accordance with FIG. 1.
Figure 3:
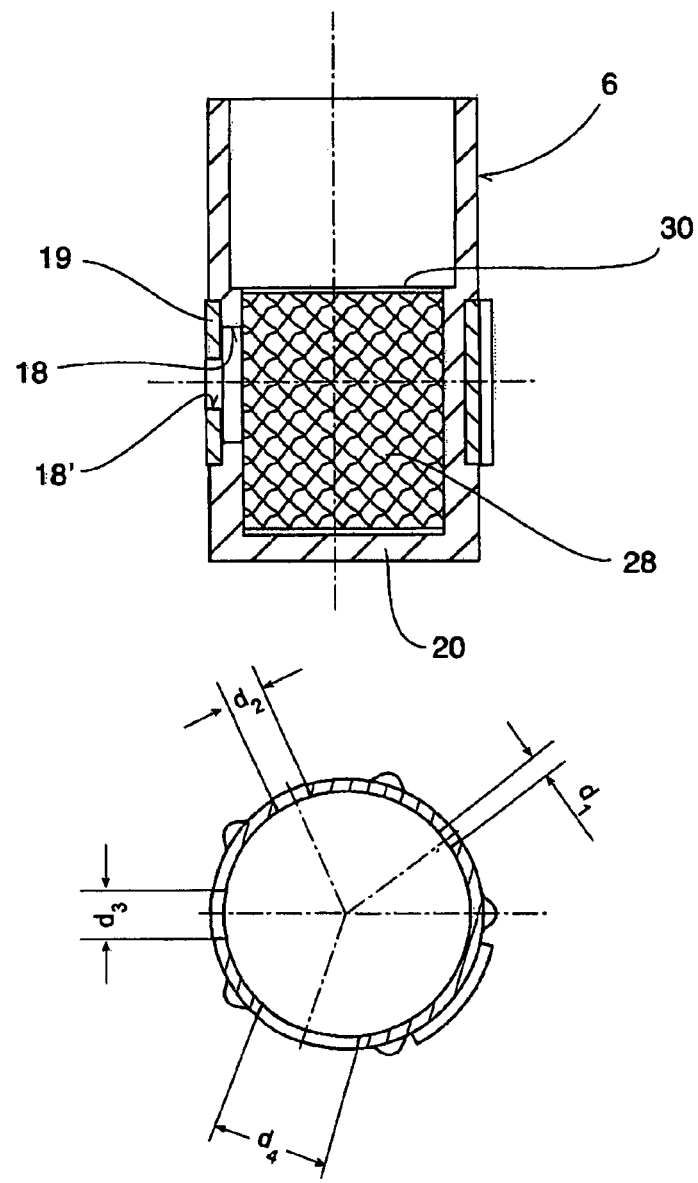
Figure 3:
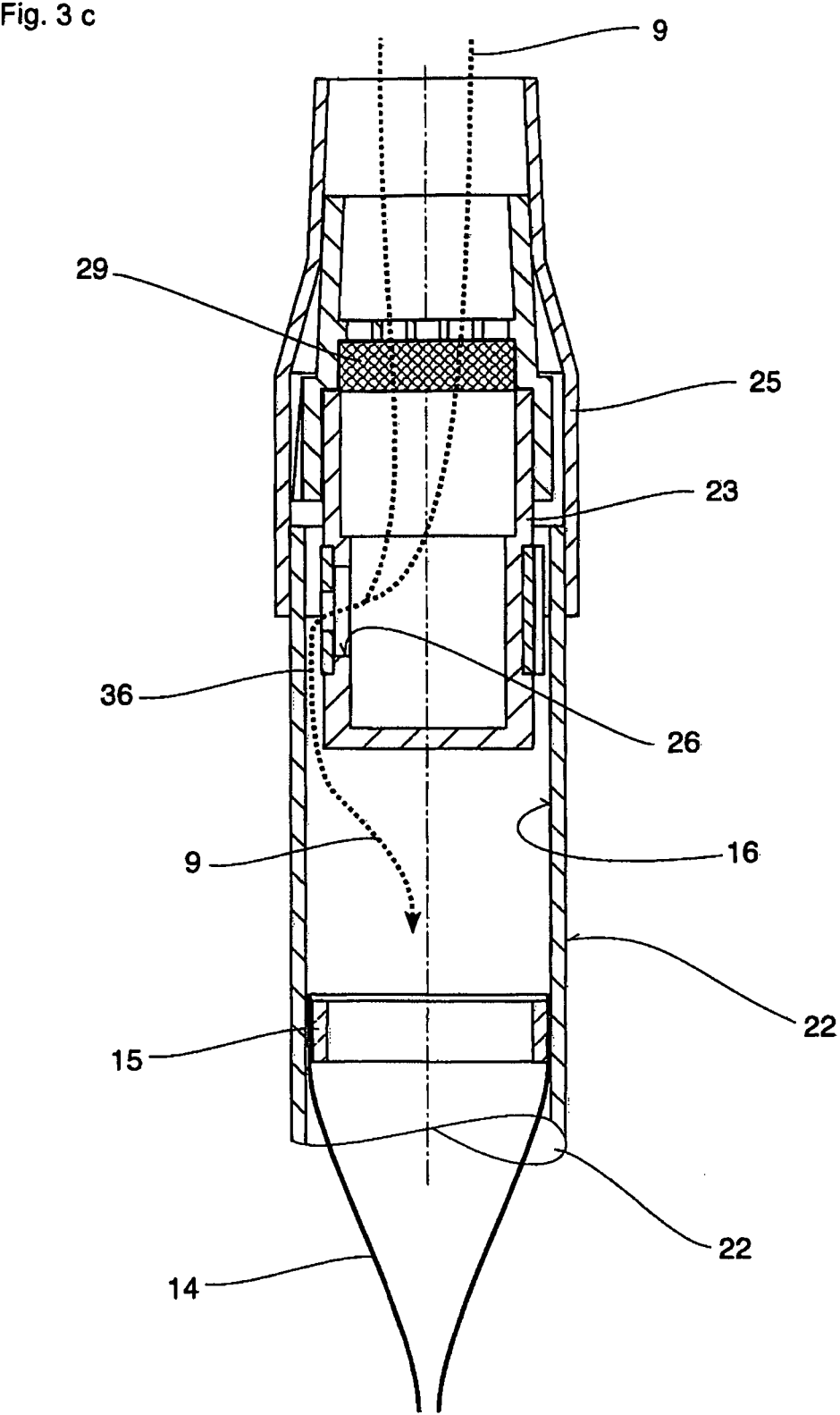

Furthermore, it is disclosed in FIGS. 1 and 3a that a ring element 17 is inserted in the first pipe section 2, between the free end 24 of the first hose 13 and the mouthpiece 6, in which case this ring element 17 has, on the one hand, four passage openings 18, or slots, disposed therein in the peripheral direction and, on the other hand, a baffle plate 20 aligned at right angles to the axis of symmetry of the pipe, by means of which baffle plate 20 the air flow inside the first pipe section 2 is deflected in the direction of the inner wall 5 of the first pipe section 2, and thus in the direction of the passage openings 18.

Moreover, an adjustable sleeve 19 is provided which has a mesh 30 in its inside on which a filter 28 is placed. As a result, the filter 28 is held by the adjustable sleeve 19. The adjustable sleeve 19 faces towards the mouthpiece 6 and is held and supported within it in a friction-locking arrangement. The mesh 30 can also be provided in the mouthpiece 6 for holding the filter 28.

The adjustable sleeve 19 allows the passage openings 18 to be fully or partially closed or fully opened, because the adjustable sleeve 19 has a circumferential collar 19' formed onto it which is provided with one or more openings 35 disposed therein with diameters of different sizes, and the inside contours of which can be configured in different ways in relation to one another. The passage openings 18 of the ring element 17 can be closed or partially opened by the collar 19', or else it is possible to provide a setting in which the passage openings 18 are fully opened when the openings 35 in the collar 19' are flush with the adjustable sleeve 19 and aligned with one or more of the passage openings 18 of the ring element 17.

The filter 28 serves to clean the air which flows through it, and to capture and hold back suspended matter or microparticles.

Furthermore, the therapeutic device 1 consists of an air distribution element 23 arranged in the second pipe section 22, the air distribution element 23 being positioned in the area of the mouthpiece 6. The air distribution element 23 is shown in particular in FIG. 3c and is provided with a ring-shaped configuration, with the effect that it corresponds to the inside contour of the mouthpiece 6 and the second pipe section 22, and can be inserted into them.

The air distribution element 23 has passage openings disposed therein with differently sized diameters, as is shown in FIG. 3b in cross section. Starting from the smallest size D1, the geometrical relationships increase to the largest diameter D4. It is possible for a plurality of differently sized passage openings 26 to be provided in the air distribution element 23.

The air distribution element 23 also has the baffle plate 20 located at right angles to the axis of symmetry of the second pipe section 22. The opposite side of the baffle plate 20 has the mesh 30 provided on it on the air distribution element, and a second filter 29 is held on the mesh 30. The mesh 30 and the filter 29 can be installed optionally for exhalation.

In accordance with FIG. 3c, the second pipe section 22 is provided with a second hose 14 inserted in it by means of a holding ring 15. The holding ring 15 is arranged at a distance from the air distribution element 23, with the effect that a sufficiently large intermediate space is provided between these two components inside the second pipe section 22.

The air distribution element 23 has a setting ring 27 allocated to it which is held on it in a rotating arrangement, and into which the openings 35 are disposed with differently sized diameters or opening widths. As a result, when the setting ring 27 is turned, it is possible for the openings 35 in the setting ring 27 to be set to different flow cross sections with the passage openings 18 provided in the air distribution element 23, with the effect that the air flowing through is partially obstructed. This is because the air flowing in should flow through them out of the air distribution element 23 into an intermediate space 36 located between an inner wall 16 of the second pipe section 22 and the air distribution element 23 or the outer circumference of the setting ring 27.

FIG. 1 shows that the second pipe section 22 has a second end 33 which can be sealed using a stopper 37 in which an opening 37' is disposed.

FIG. 2a firstly shows the inhalation procedure schematically. The flow direction established for the drawn-in air is indicated by the reference number 8. As a result, the patient uses his or her respiratory musculature to breathe in air through the first pipe section 2 which flows into the pipe section 2 in the area of the second end 4 through the inlet opening 10, and enters the first hose 13 through the passage channel 12 of the holding peg 11.

As shown by the schematic vibration arrows 8', the free end 24 of the first hose 13 is moved back and forth between the inner wall 5 of the first pipe section 2. The vibratory behaviour of the first hose 13 can be variably adjusted as a result of the different curvature of the pipe section 2 and the adjustable position of the first hose 13 relative to it. The holding peg 11 is held in a moveable arrangement in the second end 4 of the first pipe section 2, which means the length of the first hose 13 which protrudes into the first pipe section 2 can have different lengths, as a result of which the hose 13 can be kinked or bend at different points.

The air flowing in, or drawn in, causes the flexible hose 13 to expand, with the effect that the air passes through it and enters the inside of the first pipe section 2. The baffle plate 20 of the ring element 17 redirects the air outwards, i.e. in the direction of the inner wall 5, and from the baffle plate 20 the air is guided sideways in the direction of the passage opening 18 or openings 35 in the ring element 17 or the adjustable sleeve 19.

The cross sectional area set between the passage openings 18 and the openings 35 means the air resistance prevailing there is increased or reduced according to the cross sectional area through which the air flow can pass.

As soon as the air flow leaves the ring element 17 in the direction of the mouthpiece 6, it flows through the first passage channel 7 in the direction of the shared channel 21' of the channel branch 21 into the patient's mouth cavity. As a result of the air pressure situation prevailing inside the two pipe sections 2 and 22, a negative pressure is formed in the second pipe section 22, because air is drawn out of this in accordance with the air flow direction 8. This negative pressure is communicated to the second hose 14 due to the air pressure situation prevailing between the air distribution element 23 and the inside of the second pipe section 22, as a result of which a negative pressure results inside the second hose 14, causing the flexible side wall of the hose 14 to enter into contact, thereby preventing air flow through the second hose 14. As a result, the second hose 14 acts in this operating status as a kind of valve preventing air from entering through the second pipe section 22 in the direction of the mouthpiece 6.

As a result of the vibratory behaviour of the first hose 13, the patient can hear and detect that the necessary negative pressure preset by the opening width has been achieved.

FIG. 2b shows the operating status during exhalation. The flow direction of the exhaled air out of the patient's pulmonary space is identified by the reference number 9. The air flow is initially forced into the mouthpiece 6 and, there, it is distributed in the area of the air channel branch 21. The air flow which enters the second pipe section 22 is forced through the passage openings 26 into the intermediate space 36 and, from there, it enters the inside of the second pipe section 22, and thus into the second hose 14 which is now expanded by the air flow and is, in its turn, induced to adopt an oscillating vibratory behaviour if a sufficiently high air pressure is generated by the air that is forced in.

The air flowing out through the second hose 14 is evacuated into the atmosphere through the second end 33 and the opening 37' in the stopper 37.

The other portion of the exhaled air flow enters the first pipe section 2 and, there, it initially exits the ring element 17 through the passage openings 18 and enters the inside of the first pipe section 2. There is a positive pressure in this pipe section 2 due to the air flowing in, as a result of which the first hose 13 is compressed and thereby closes like a kind of valve, with the effect that no air can escape from the inside of the first pipe section 2.

The positive pressure prevailing in the first pipe section 2 therefore leads to the situation that a correspondingly formed cushion of air prevails immediately after exhalation, by means of which the exhaled air is directed into the second pipe section 22 after a certain period of time, at least in its entirety. The first and second pipe sections 2 and 22 can be provided with separate mouthpieces 6 and consequently can be used independently of one another.

The invention claimed is:

1. A therapeutic device for improving respiration of a person, the device comprising a curved or kinked pipe section, into a first end of which a mouthpiece provided with a passage channel is disposed, with a holding peg inserted into a second end of the pipe section and connected to it, the holding peg having a passage channel disposed therein and insertable in whole and in part into the pipe section, and a flexible hose attached to the holding peg inside the pipe section, with a free end of the hose moveable freely in an area of the mouthpiece within an inner wall of the pipe section,
wherein
a channel branch emerges into the passage channel of the mouthpiece and is provided with a second pipe section connected therein, and the second pipe section is provided with an air distribution element disposed therein, into the outside circumference of which at least one passage opening is disposed, the width of which can be variably adjusted by means of a setting ring.

2. The therapeutic device in accordance with claim 1, wherein
a flexible hose behind the air distribution element in a flow direction is disposed in the second pipe section, by means of which an air flow through the air distribution element is guided, and as a result of which the hose is induced to vibrate.

3. The therapeutic device in accordance with claim 2, wherein
the hose on the air distribution element is locked directly or by means of a holding ring against an inside wall of the second pipe section.

4. The therapeutic device in accordance with claim 1, wherein
the air distribution element is provided with a filter disposed therein, through which air flow flows, and the filter lies on a mesh or perforated plate of the air distribution element and is supported thereby.

5. The therapeutic device in accordance with claim 1, wherein
the air distribution element is provided with a covering ring, which can be rotated in a peripheral direction of said air distribution element and by means of which the passage opening disposed in the air distribution element is fully or partially closed or fully opened.

6. The therapeutic device in accordance with claim 1, wherein
said pipe section is provided with a ring element therein in the area of an end facing towards the mouthpiece, at least one passage opening is disposed in the ring element and an adjustable sleeve is folded over the ring element in the installed condition, by means of which a corresponding passage opening is fully or partially closed or fully opened.

7. The therapeutic device in accordance with claim 6, wherein
a baffle plate is formed onto the ring element, by means of which air flow is blocked in the direction of said pipe section.

8. The therapeutic device in accordance with claim 1, wherein
a distance between the free end of the hose and the mouthpiece inserted disposed in the pipe section is variably adjustable by moving the holding peg in order to change the curvature radius of the hose.

9. The therapeutic device in accordance with claim 2, wherein
a negative pressure is produced in the inside of the second pipe section during inhalation, by means of which the second hose inside the second pipe section is induced to vibrate and, at the same time.

10. The therapeutic device in accordance with claim 1, wherein
during exhalation, the first hose is closed by means of positive pressure prevailing in the pipe section.

11. A therapeutic device for improving the respiration of a patient, the device comprising a curved or kinked pipe section, into a first end of which a mouthpiece is disposed, with a holding peg inserted into the first end of the pipe section and held in a movable arrangement, with a flexible hose attached to an end of the holding peg and pointing away from the mouthpiece, with the flexible hose following the curvature of the pipe section,
wherein
the holding peg is configured as an air distribution element, at least one passage opening is disposed in the air distribution element, and the passage opening is adapted to be fully or partially closed or completely opened by means of an adjusting ring.

* * * * *